(12) United States Patent
Berry

(10) Patent No.: US 12,128,156 B2
(45) Date of Patent: Oct. 29, 2024

(54) DUAL MATERIAL IMPLANT

(71) Applicant: Phoenyx Spinal Technologies, Inc., Tallahasee, FL (US)

(72) Inventor: Bret Michael Berry, Tallahassee, FL (US)

(*) Notice: Subject to any disclaimer, the term of this patent is extended or adjusted under 35 U.S.C. 154(b) by 262 days.

(21) Appl. No.: 17/012,350

(22) Filed: Sep. 4, 2020

(65) Prior Publication Data

US 2022/0072205 A1   Mar. 10, 2022

(51) Int. Cl.
*A61L 27/56* (2006.01)
*A61L 27/12* (2006.01)
*A61L 27/18* (2006.01)

(52) U.S. Cl.
CPC .......... *A61L 27/56* (2013.01); *A61L 27/12* (2013.01); *A61L 27/18* (2013.01); *A61L 2300/412* (2013.01); *A61L 2430/02* (2013.01); *A61L 2430/38* (2013.01)

(58) Field of Classification Search
CPC .......... A61L 27/12; A61L 27/16; A61L 27/18; A61L 27/56; A61L 2300/412; A61L 2430/02; A61L 2430/38; C08L 33/12; C08L 71/12
See application file for complete search history.

(56) References Cited

U.S. PATENT DOCUMENTS

2006/0224242 A1* 10/2006 Swords .............. A61B 17/8085
606/915

FOREIGN PATENT DOCUMENTS

| EP | 3666231 | * | 6/2020 |
| TW | 200304368 A | * | 10/2003 |
| WO | WO 2010007424 | * | 1/2010 |

* cited by examiner

*Primary Examiner* — Lezah Roberts
(74) *Attorney, Agent, or Firm* — McCarter & English, LLP; James M. Smedley; Alex Korona

(57) ABSTRACT

The present invention generally relates to an orthopedic implant. Specifically, the present invention relates to an implant that incorporates a purposefully designed material that optimizes bony ingrowth combined with a support material configured to provide structural integrity.

15 Claims, 8 Drawing Sheets

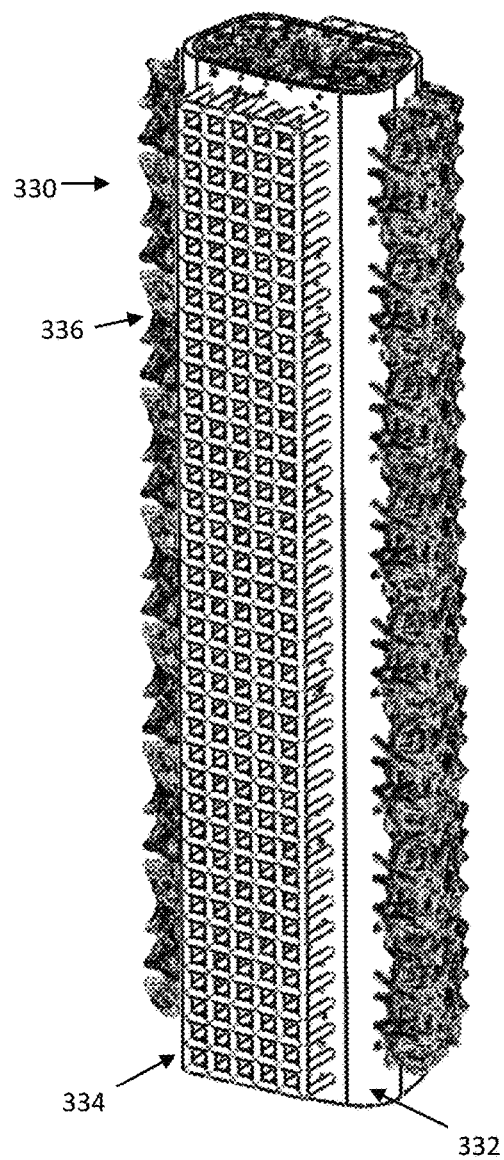
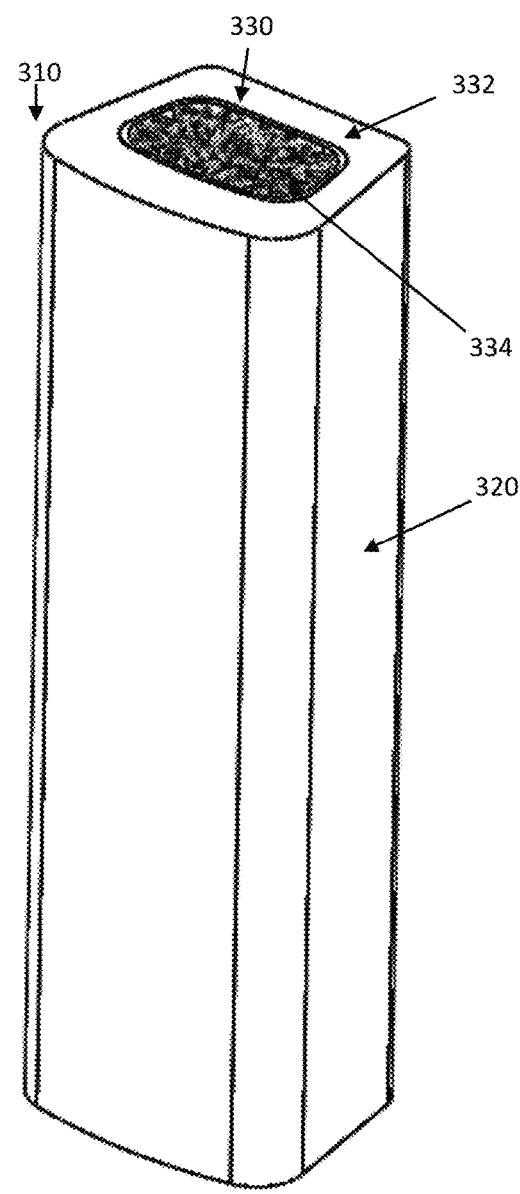
FIG. 13
FIG. 14

DUAL MATERIAL IMPLANT

FIELD OF THE INVENTION

The present invention generally relates to an orthopedic implant. Specifically, the present invention relates to an implant that incorporates a purposefully designed material that optimizes bony ingrowth combined with a support material configured to provide structural integrity.

BACKGROUND OF THE INVENTION

Orthopedic implants are commonly used in a variety of orthopedic applications. While the structure of an implant is primarily based on application, a primary consideration for any implant is achieving a design the maximizes strength, while also promoting bone growth to achieve proper fusion between the implant and adjacent bone(s). Accordingly, implant designs have incorporated both nonporous and porous structures, with the goal of having the nonporous areas providing strength and structural support to the implant and the porous areas promoting bone growth and fusion.

Traditionally, a single material is used to form an orthopedic implant which includes a porous section and a solid section. For example, titanium metal has been used to form implants to provide both a porous section for bony ingrowth and a solid section for structural strength. However, titanium implants and implants formed from similar metal materials have a number of drawbacks including, that they have a high modulus of elasticity which inhibits bone growth, and that they are typically highly radio-opaque, preventing post-operative examination of bone growth with imaging technology.

Therefore, there is a need in the art for an implant and related manufacturing method that can, within a single implant, incorporate both solid nonporous and porous sections to provide both adequate structural support and promote optimal bone growth and fusion. The present invention is provided to solve the problems discussed above and other problems, and to provide advantages and features not provided by currently available implants. These and other features and advantages of the present invention will be explained and will become obvious to one skilled in the art through the summary of the invention that follows.

SUMMARY OF THE INVENTION

Accordingly, embodiments of the present invention are directed to an orthopedic implant with a first implant material optimized for bony ingrowth combined with a second implant material that provides structural support.

Embodiments of the present invention contemplate a first implant material comprising a bony ingrowth material engineered as a tubular network that forms one or more three-dimensional ("3D") matrixes, which provide a porous region at any desired location within an implant and with any desirable pore structure, size, or porosity. The contemplated 3D matrix or matrixes may be formed of an osteo-conductive material or coated or infused with an osteo-conductive substance. The second implant material comprising a radiolucent support material may be formed with or added to the first implant material to provide structural support to the implant while permitting radio-lucency.

The foregoing summary of the present invention with the preferred embodiments should not be construed to limit the scope of the invention. It should be understood and obvious to one skilled in the art that the embodiments of the invention thus described may be further modified without departing from the spirit and scope of the invention. Other features and advantages of the invention will be apparent from the following specification taken in conjunction with the following drawings. While many materials and methods of design have been attempted, a number of drawback and limitations prevent an optimal design.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

FIG. 13 shows a perspective view of a porous section of a stock rod used to create a dual material implant in accordance with a third exemplary embodiment of the present invention.

FIG. 14 shows a perspective view of a stock rod used to create a dual material implant in accordance with a third exemplary embodiment of the present invention.

DETAILED DESCRIPTION

Figure 1:
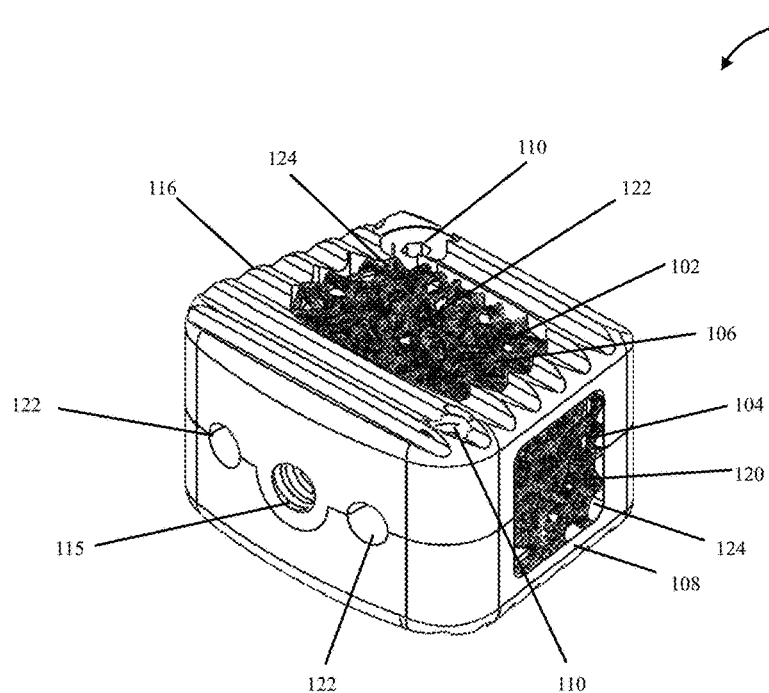
FIG. 1 shows a perspective view of a dual material implant in accordance with a first exemplary embodiment of the present invention.

The present invention generally relates to an orthopedic implant. Specifically, the present invention relates to an implant that incorporates a purposefully designed material that optimizes bony ingrowth combined with a support material configured to provide structural integrity.

According to an embodiment of the present invention, an orthopedic implant may comprise a first implant material comprising a bony ingrowth section engineered as a 3D matrix configured with a network of interconnected hollow tubes formed of ϴ-tricalcium phosphate ("β-TCP"), hydroxyl apatite ("HA"), or other natural bone ingrowth materials or a combination thereof, that provide a porous region within the implant for bony ingrowth, and a second implant material comprising a support material formed of polyether ether ketone ("PEEK") or polyether ether ketone-hydroxyl apatite ("PEEK-HA") that is formed with, added to, combined with, or otherwise coupled to the first implant material to provide structural support for the implant.

According to an embodiment of the present invention, an orthopedic implant includes a first implant material and a second implant material combined to form a substantially stable and structurally sound implant which in configured to promote bony ingrowth. In an exemplary embodiment, β-TCP, HA, or other natural bone growth material, or a combination of any of the foregoing may be used to form the first implant material which may include one or more hollow 3D matrixes having a network of continuously interconnected tubes to provide a porous region in the implant into which bone can grow. The first implant material may be combined or added to a second implant material that provides structural support to the implant such as PEEK, PEEK-HA, or titanium. In some embodiments, the first implant material and/or the 3D matrixes disposed therein may be made from or coated with hydroxyl apatite ("HA") due to its osteo-conductive properties. However, any variety of osteo-conductive materials could be used for the first implant material, including, but not limited to, various bioactive glasses. The material used to provide structural support to the implant is preferably PEEK, but could formed of other biocompatible or radiolucent materials, or a combination of PEEK and any such biocompatible or radiolucent materials. The use of PEEK for structural support section of the implant is advantageous because PEEK has an elastic modulus that is similar to bone and is radiolucent, making it easier to observe bone growth and fusion within and around the implant. Other materials may be incorporated into the support structure material, including, but not limited to, HA, bioactive glasses, and any combination thereof, to further enhance the stimulation of bony ingrowth while permitting radio-lucency. One of ordinary skill in the art would appreciate that there are many other materials or combination of materials from which an orthopedic implant could be fabricated, and embodiments of the present invention are contemplated for use with any such material or combinations of materials.

According to an embodiment of the present invention, the 3D matrixes may be 3D printed, thereby allowing the creation of a precise structure. In some examples, 3D printing is capable of repeatedly creating 3D matrixes with identical specifications, including, but not limited to 3D matrixes with the same dimensions, pore structure, porosity, and pore size, with the only limitation on the implant design and size being the size of the machinery producing it. Additionally, each of these methods is capable of creating the porous structure within any section of the implant and at any depth. One of ordinary skill in the art would appreciate there are a variety of methods for implementing the 3D printing technique, and embodiments of the present invention are contemplated for use with any such methods.

According to an embodiment of the present invention, a 3D matrix may be a network of continuously connected tubes. Each of the hollow tubes may have a diameter between 0.5 mm and 1.0 mm. In some embodiments, however, the tubes may be smaller than 0.5 mm or larger than 1.0 mm. In an exemplary embodiment, each tube of the 3D matrix may intersect with another tube of the 3D matrix every 3.0 mm to 4.0 mm. Each tube may proceed uninterrupted for a length of approximately 3.0 mm to 4.0 mm before intersecting with another tube, however the interval may be longer or shorter depending upon the intended application of the implant. In some scenarios, the tubes of the 3D matrix are not in straight lines, but have curves, twists, angles, and other changes of direction, as this has been shown to improve bone growth and fusion. However, the 3D matrix could be configured with straight line tube structures if beneficial for a particular application. Additionally, the internal surface of the tubes of the 3D matrix may be roughened, to improve the growth and fusion of the bone tissue. One of ordinary skill in the art would appreciate that 3D matrix could be precisely designed with a tubular structure based upon the intended application or purpose of the implant, and embodiments of the present invention are contemplated for use with any such design.

According to an embodiment of the present invention, the first implant material may include a 3D matrix having a varying tubular structure thereby creating a variable porosity, or amount of hollow space, within the implant. Generally, the overall porosity of a given implant will be determined by the amount of hollow space in the first or second implant material. In some scenarios, the porosity of the first or second implant material may be specifically tailored based upon the application and purpose of the implant. Furthermore, the first or second implant materials or both may have multiple individual hollow 3D matrixes positioned in different portions of the respective implant materials. In this way, a given implant need not have a consistent porosity throughout, but instead could have a varying porosity in different sections of the implant to promote bone growth, or otherwise as necessary for a particular application of the implant. The customizable nature of the first and second implant materials, along with the variable design and placement of a 3D matrix within an implant, allows for an implant to configured in accordance with the intended application for the implant. Notably, the overall porosity of two different implants could be the same despite having vastly different design objectives. In some examples, the porosity of the implant may be approximately 50%, but may vary within an ideal range of between 20 to 80%.

Figure 2:
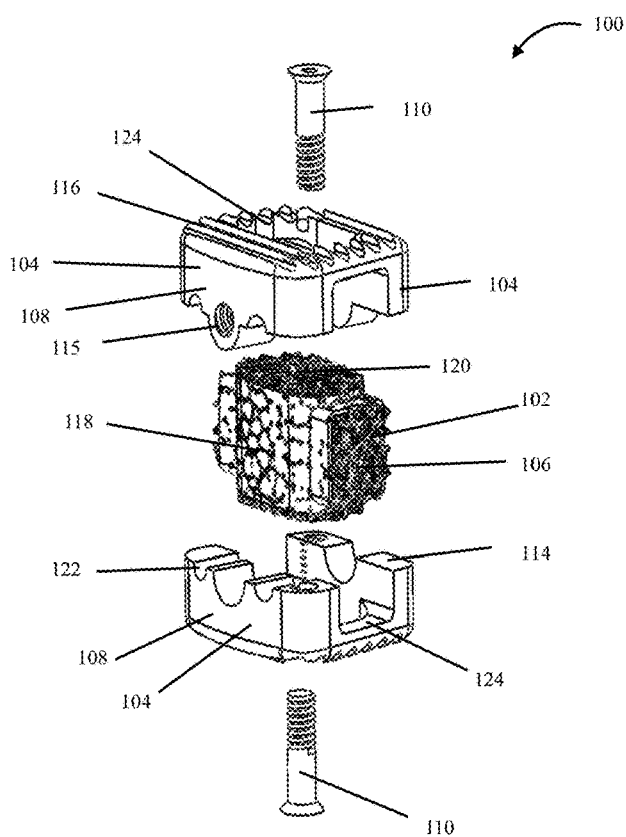
FIG. 2 shows an exploded view of a dual material implant in accordance with a first exemplary embodiment of the present invention.
Figure 3:
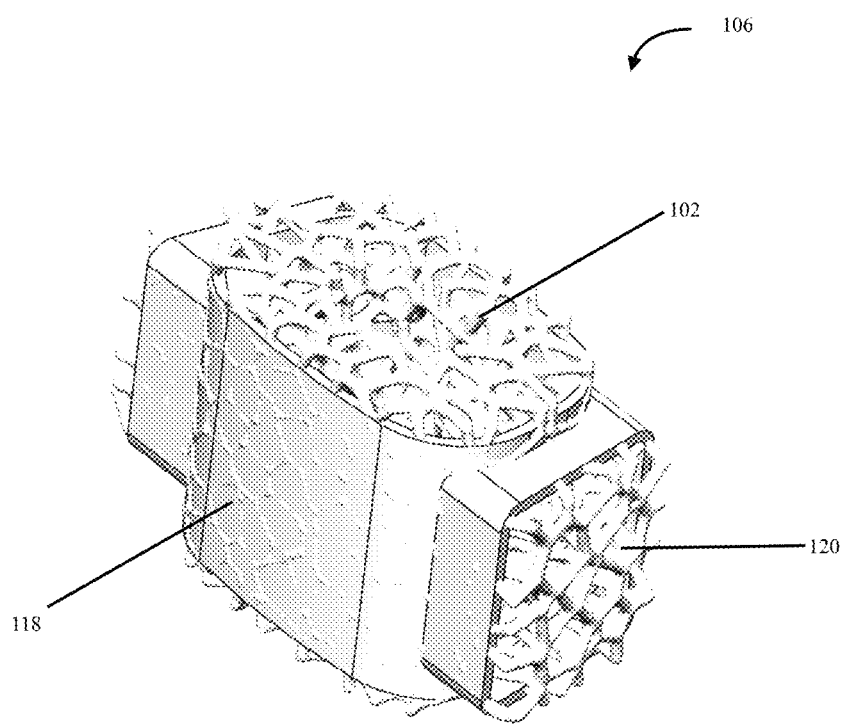
FIG. 3 shows an exemplary configuration of a porous implant section of a dual material implant in accordance with a first exemplary embodiment of the present invention.

FIGS. 1-3 generally show a first exemplary embodiment of the present invention wherein the porous section and the support section of the implant are configured to be mechanically joined, for example, by enclosing the implant support section about or around the porous implant section.

FIG. 1 shows a perspective view of a dual material implant in accordance with a first exemplary embodiment of the present invention. As shown in FIG. 1, according to an embodiment of the present invention, the implant 100 may include a first implant material 102 added to or combined with a second implant material 104 which is configured to provide structural strength to the implant 100 while permitting its radio-lucency. In some embodiments, the first and second implant materials 102 and 104 may be 3D printed simultaneously to form a singular implant 100. For example, the first and second implant materials 102 and 104 may be 3D printed by a specialized printer with dual application nozzles. The materials used to create the 3D printed structure may include thermoplastics or ceramics, for example, zirconia or alumina. In some embodiments, the first implant material 102 may be 3D printed into the second implant material 104. In some embodiments, the second implant material 104 comprises an implant support section 108 comprising a support material, for example, PEEK or PEEK-HA, and is added to or combined with a porous implant section 106 comprising a first implant material 102 formed of, for example, β-TCP, HA, or other natural bone growth material, through mechanical means, for example, by press fitting the porous implant section 106 into the implant support section 108 and/or through the use of adhesives or fasteners such as screws or pins. In some examples, the implant support section 108 may be welded to the porous implant section 106, for example, if the sections comprise metal elements. In some scenarios, the implant support section 106 may be ultrasonically welded to the porous implant section 106, for example, if the sections comprise plastic elements. In some examples, the second implant material 104 of the implant support section 108 is configured to be enclosed upon the first implant material 102 of the porous implant section 106. In some embodiments, the support section 108 may be overmolded onto the porous section 106.

FIG. 2 shows an exploded view of a dual material implant in accordance with a first exemplary embodiment of the present invention. As shown in FIG. 2, the implant support section 108 may be comprised of one or more support units 112 which are configured to connect with one another to enclose the porous implant section 106. In the depicted example, titanium screws 110 connect the support units 112 of the implant support section 108 to enclose the porous implant section 106. Each of the support units 112 are configured to maintain the structural integrity of the implant 100 during and after implantation. In the illustrated example, the implant support section 108 is comprised of two support units 112 which are configured to connect with one another in a manner that encloses the porous implant section 106. One or more outer walls of the support unit 112 may include a support unit mating surface 114, for example, to promote the connection of a first support unit 112 to a second support unit 112. For example, the support unit mating surface 114 of a first support unit 112 may have bulges, divots, notches, protrusions or indentations which correspond to bulges, divots, notches, protrusions or indentations in the support unit mating surface 114 of a second support unit 112. In some examples, the support unit mating surfaces 114 of the support units 112 ease the assembly process of the implant 100 and enhance the torsional strength of an inserted implant 100 during and after implantation.

In some embodiments, the support section 108 of the implant 100 includes one or more inserter apertures 115. In some embodiments, the inserter apertures 115 are configured to engage with an inserter (not shown). In some embodiments, an inserter (not shown) is used to connect to and hold the implant 100 while the implant 100 is inserted into a patient body during a given procedure.

FIG. 3 shows an exemplary configuration of a porous implant section of a dual material implant in accordance with a first exemplary embodiment of the present invention. As shown in FIG. 3, according to embodiments of the present invention, the porous implant section 106 may have one or more solid or non-porous exterior walls 118. In some scenarios, the non-porous exterior walls 118 of the porous implant section 106 are configured to a provide a durable mating surface against the inner walls of the implant support section 108 and prevent the fracture of the exterior walls of the porous implant section 106. For example, the non-porous exterior walls 118 of the porous implant section 106 may be configured to prevent the possible fracture of the thin struts that make up the porous portion of the porous implant section 106. In some examples, the non-porous exterior walls 118 of the porous implant section 106 are resilient and durable to prevent fracture of the porous implant section 106 during impaction of an implant 100 into the disc space of a patient.

FIGS. 4-12 generally show a second exemplary embodiment of the present invention wherein the implant support section is configured to be overmolded onto or around the porous implant section of the implant.

Figure 4:
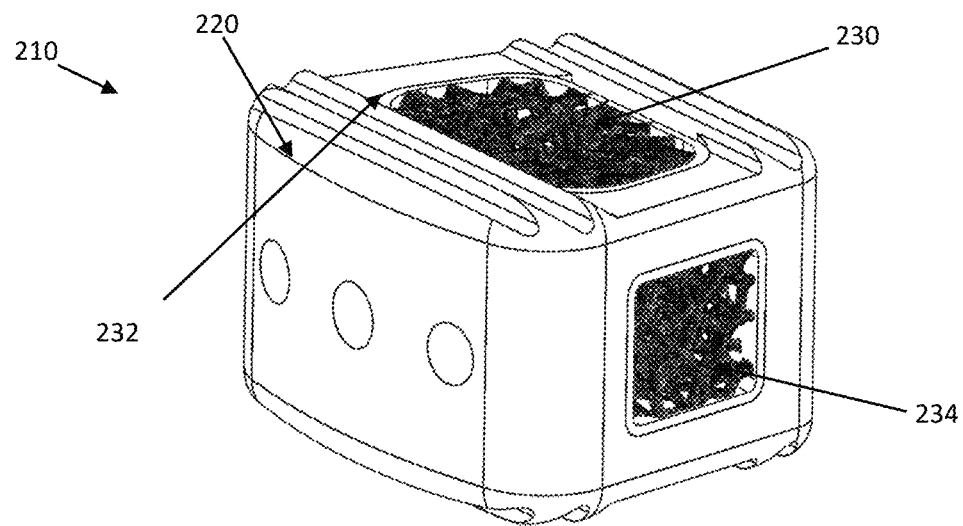
FIG. 4 shows a perspective view of a dual material implant in accordance with a second exemplary embodiment of the present invention.

FIG. 4 shows a perspective view of a dual material implant in accordance with a second exemplary embodiment of the present invention. As shown in FIG. 4, the implant 200, may be comprised of an implant support section 220 and a porous implant section 230. The implant support section 220 may be overmolded onto the porous implant section 230, to create the implant 200. In some examples, the implant 200 may be molded into a final, as-is implant. In any embodiment, the implant support section 220 may be formed of PEEK, HA-Enhanced PEEK, Carbon reinforced PEEK, poly(methyl methacrylate) (PMMA), or any other suitable material which can be injection molded.

Figure 5:
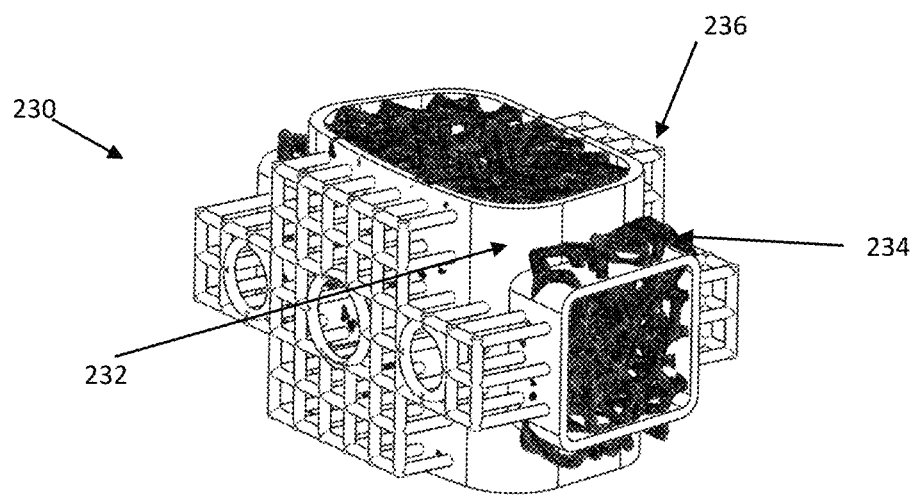
FIG. 5 shows a perspective view of a porous section of a dual material implant in accordance with a second exemplary embodiment of the present invention.

FIG. 5 shows a perspective view of a porous section of a dual material implant in accordance with a second exemplary embodiment of the present invention. The porous implant section 230 may be a 3D printed structure and may be comprised of a solid wall portion 232. The solid wall portion 232 may be configured to prevent the passage of the material of the implant support section 220. In some examples, the solid wall portion 232 may ensure that the implant support section 220 does not penetrate into the porous bone growth structure 234 of the porous section 230. The porous bone growth structure 234 may be a tight, randomized lattice that may be optimized for bony ingrowth. Although the porous bone growth structure 234 may be an open cell structure, it is unlikely that the injection molded material of the implant support section 220 would penetrate too deep into the lattice, merely due to the viscosity of the material, and the small pore size required for optimal bony ingrowth. However, the solid wall 232 may be necessary to keep as much of porous bone growth structure 234 unfilled and available for bone growth. The porous bone growth structure 234 may be generally surrounded by the solid wall 232, however, the porous bone structure 124 may protrude outside of the solid wall 232.

Figure 6:
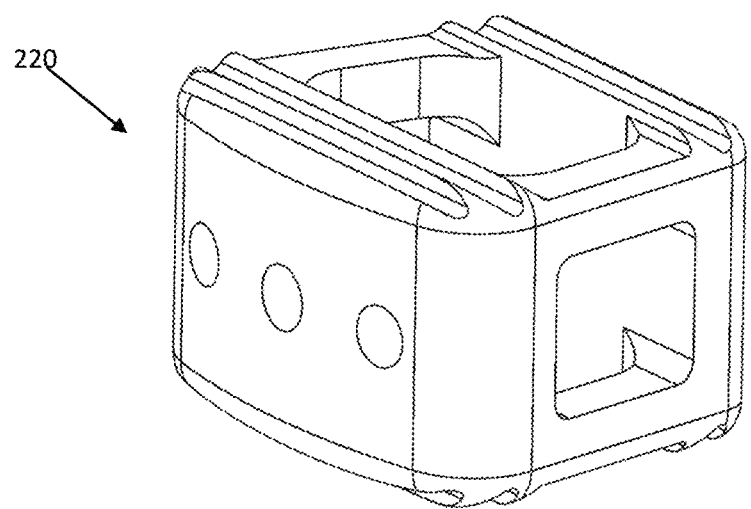
FIG. 6 shows a perspective view of support section of a dual material implant in accordance with a second exemplary embodiment of the present invention.
Figure 7:
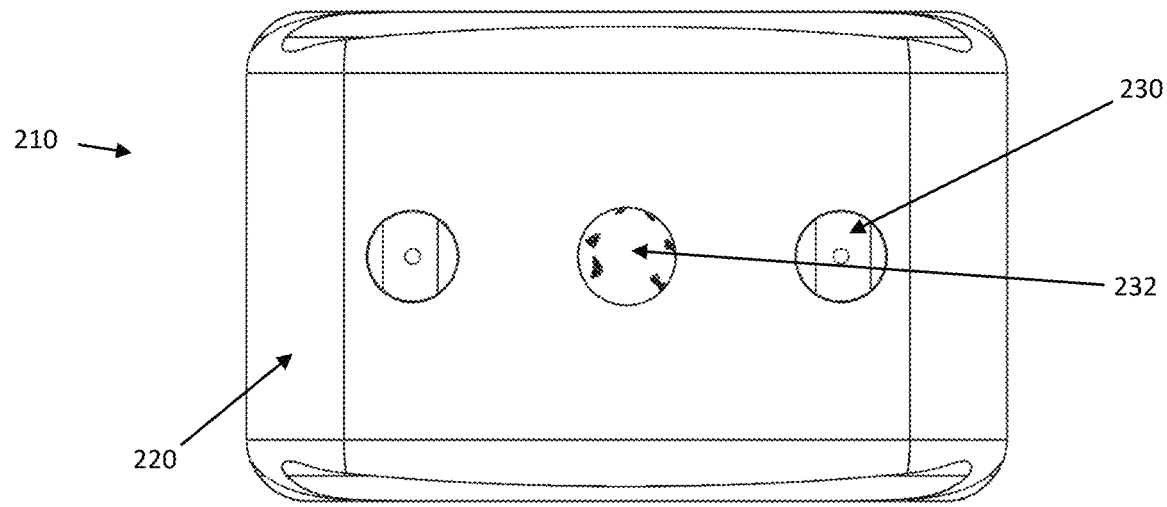
FIG. 7 shows a front view of a dual material implant in accordance with a second exemplary embodiment of the present invention.
Figure 8:
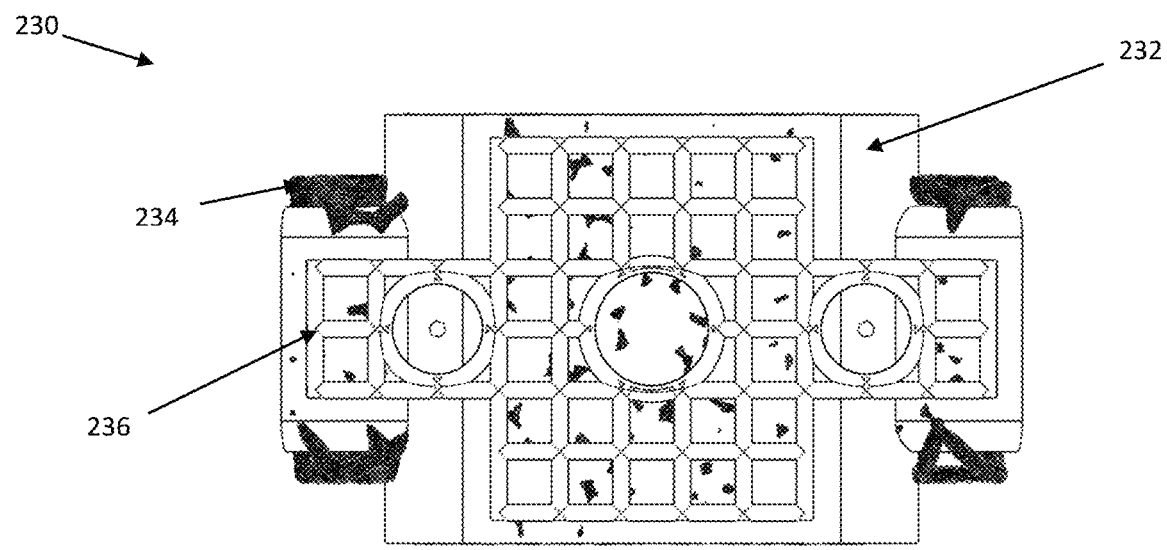
FIG. 8 shows a front view of insert component a dual material implant in accordance with a second exemplary embodiment of the present invention.
Figure 9:
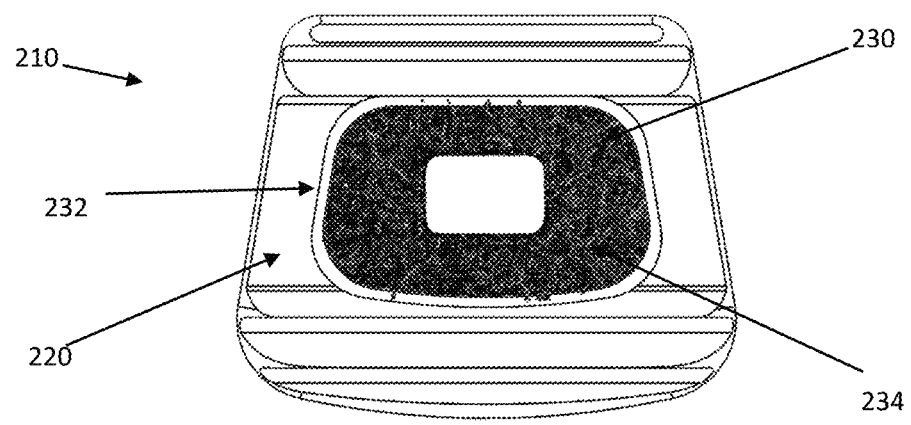
FIG. 9 shows a top view of a dual material implant in accordance with a second exemplary embodiment of the present invention.
Figure 10:
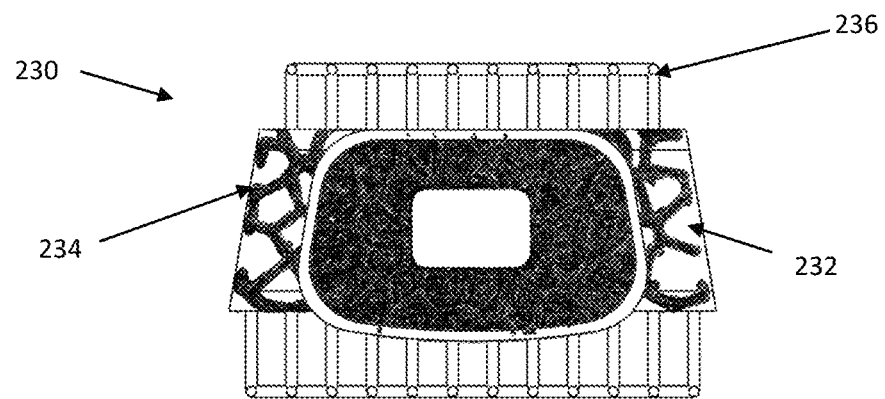
FIG. 10 shows a top view of a porous section of a dual material implant in accordance with a second exemplary embodiment of the present invention.
Figure 11:
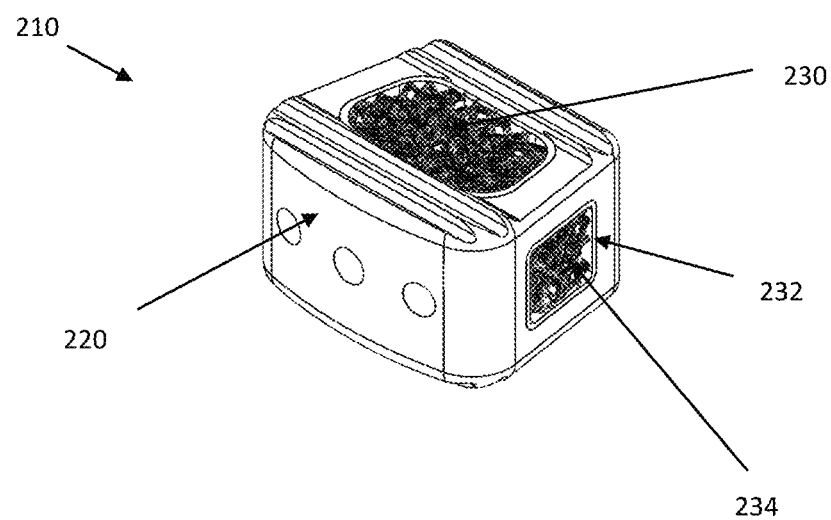
FIG. 11 shows a perspective view of a dual material implant in accordance with a second exemplary embodiment of the present invention.
Figure 12:
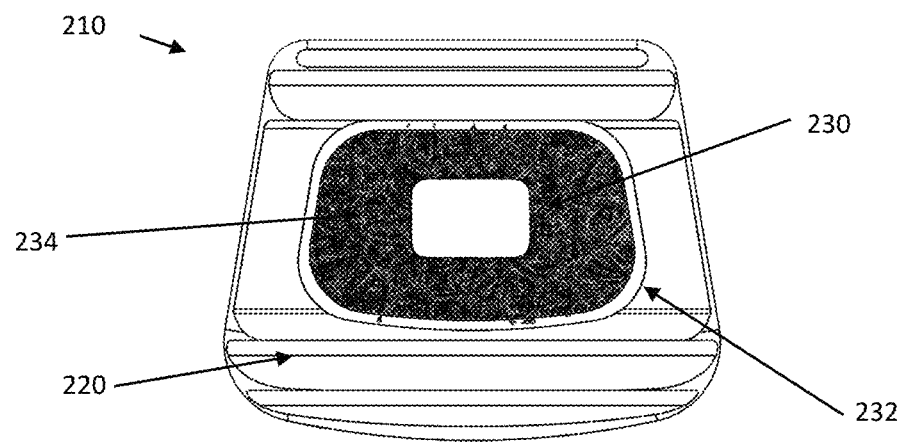
FIG. 12 shows a top view of a porous section of a dual material implant in accordance with a second exemplary embodiment of the present invention.

FIG. 6 shows a perspective view of support section of a dual material implant in accordance with a second exemplary embodiment of the present invention. The implant support section 220 may be overmolded onto the porous implant section 230, to create the implant 200. The implant support section 220 may be formed of PEEK, HA-Enhanced PEEK, Carbon reinforced PEEK, PMMA, or any other suitable material which can be injection molded.

FIGS. 7-12 show additional views of a dual material implant in accordance with a second exemplary embodiment of the present invention. As shown in FIGS. 7-11, the porous implant section 230 may have a porous mating structure 236 on the exterior portion of the solid wall 232. The porous mating structure 236 may be a large, open cell lattice which may have large enough pores to allow the material of the implant support section 220 to easily and fully penetrate the structure. Additionally, the porous mating structure 236 may allow the implant support section 220 and the porous implant section 230 to be permanently attached to create the implant 210. In any embodiment, the porous implant section 230 may be formed of tri-Calcium Phosphate, HA, PMMA, or any other material which can be 3D printed.

FIGS. 13-14 generally show a third exemplary embodiment of the present invention wherein the support section is overmolded onto the porous section to form a stock rod capable of forming one or more implants.

FIG. 13 shows a perspective view of a porous section of a stock rod that may be used to create a dual material implant in accordance with a third exemplary embodiment of the present invention. As shown in the depicted example, the stock rod 310 may be comprised of an implant support section 220 and a porous implant section 330. The implant support section 320 may be overmolded onto the porous implant section 330, to create the stock rod 310. The stock rod 310 may be molded into an elongated stock shape, which can then be machined into one or more final implants. In some scenarios, individual molds may be expensive to formulate, and given the plethora of shapes and sizes used in spinal implants, it may be cost prohibitive to have individual molds for each footprint and height which is sometimes required. The stock rod 310 solves these and other issues by allowing for fewer molds to be created, thereby reducing costs. The stock rod 310 may be cut into multiple implants of various heights. The implant support section 320 may be formed of PEEK, HA-Enhanced PEEK, Carbon reinforced PEEK, PMMA, or any other material which can be injection molded.

FIG. 14 shows a perspective view of a stock rod used to create a dual material implant in accordance with a third exemplary embodiment of the present invention. The porous implant section 330 may be a 3D printed structure and may be comprised of a solid wall portion 332, which may be configured to prevent the passage of the material of the implant support section 320. The solid wall portion 332 may be configured to ensure that the implant support section 320 does not penetrate into the porous bone growth structure 334 of the porous implant section 330. The porous bone growth structure 334 may be a tight, randomized lattice that may be optimized for bony ingrowth. Although the porous bone growth structure 334 may be an open cell structure, it is unlikely that the injection molded material of the implant support section 320 would penetrate too deep into the lattice, merely due to the viscosity of the material, and the small pore size required for optimal bony ingrowth. However, the solid wall 332 may be necessary to keep as much of porous bone growth structure 334 unfilled and available for bone growth. The porous bone growth structure 334 may be generally surrounded by the solid wall 332, however, it may protrude outside of the solid wall 332. The porous implant section 330 may have a porous mating structure 336 on the exterior portion of the solid wall 332. The porous mating structure 336 may be a large, open cell lattice which may have large enough pores to allow the material of the implant support section 320 to easily and fully penetrate the structure. Additionally, the porous mating structure 336 may allow the implant support section 320 and the porous implant section 330 to be permanently attached to create the stock rod 310. The porous implant section 330 may be formed of tri-Calcium Phosphate, HA, PMMA, or any other material which can be 3D printed.

In accordance with embodiments of the present invention, a porous implant section 106 including one or more 3D hollow matrixes 120 may be substantially comprised of a first implant material 102 for the promotion of bony ingrowth while an implant support section 108 may be substantially comprised of a radiolucent second implant material 104 configured to provide structural integrity and support to permit post-operative examination of bone growth with imaging technology. In some instances, the combination of a porous first implant material 102 and a substantially sturdy and generally nonporous second implant material 104 provides an implant having a solid, weight-bearing support section 108 adjacent to a substantially porous section 106 that supports bone growth and fusion which may allow for optimal imaging radio-lucency, a higher modulus of elasticity for the porous section 106 to promote the bone ingrowth capabilities of the implant 100. One of ordinary skill in the art would appreciate the implant of the present invention could be configured with any suitable porosity percentage, and embodiments of the present invention are contemplated for use with any such porosity percentage.

According to embodiments of the present invention, the implant 100 may be configured with a first implant material 102 adapted for optimal bony ingrowth combined with a second implant material 104 adapted to provide structural support to the otherwise weaker or more fragile first implant material. For example, the first implant material 102 may be HA or natural bone configured to promote bone ingrowth, and the second implant material 104 may be PEEK, PEEK-HA, or titanium, configured to provide structural support to the first implant material which typically lacks strength, for instance, during implantation of the implant 100. Moreover, once the implant is implanted into a body, the first implant material alone generally would not be able to withstand some of the natural forces expected to act on the implant, such as, for example, flexion and torsion.

In accordance with embodiments of the present invention, the size, weight, and porosity ratio of the first implant material 102 to the second implant material 104, as well as the arrangement of the first implant material 102 and the second implant material 104, are determined by the intended application for the implant 100. For example, an implant for use in the spine may have a different design than one intended for use in the hip. Additionally, the second implant material 104 of the implant 100 may be designed and arranged to provide structure and load bearing support, while the first implant material 102, formed in some instances with a substantially hollow 3D matrix 120, may provide bone growth and fusion functionalities. One of ordinary skill in the art would appreciate that there are many suitable designs and arrangements for the first and second implant materials of the proposed implant, and embodiments of the present invention are contemplated for use with any such design or arrangement.

As shown in FIGS. 1 and 2, according to an embodiment of the present invention, the implant 100 may be configured with ridged or textured areas on the outer surfaces of the implant. In the depicted example, the support section 108 includes one or more ridged surfaces 116. In some embodiments, the ridged surfaces 116 enable the implant to bite or grip onto bone neighboring the implantation area, thereby preventing unwanted migration or movement of the implant. The ridged or textured area may be formed in any suitable configuration, including, but not limited to, corrugated patterns, diamond patterns, pyramid shapes, or any combination thereof. Additionally, in embodiments where the second implant material 104 of the implant 100 is on the outer surface, the second implant material 104 could also function as the ridged or textured areas. One of ordinary skill in the art would appreciate that there are many ways to configure a ridged or textured area on an implant to prevent unwanted migration and movement, and embodiments of the present invention are contemplated for use with any such configuration.

According to an embodiment of the present invention, the implant 100 may be configured with one or more cavities 122 in one or more walls of the first or second implant materials 102 and 104. In some embodiments, a cavity 122 may be a channel that goes entirely through a wall of the implant 100. A cavity 122 may be added to the implant 100 to adapt the implant 100 to a certain application or to improve the performance of the implant 100. One of ordinary skill in the art would appreciate that there are many suitable designs and layouts for incorporating cavities into the walls of the implant, and embodiments of the present invention are contemplated for use with any such cavity design and layout.

As shown in FIGS. 1 and 2, in some embodiments, one or more walls of the support section 108 may include one or more hollow recesses 124 configured to provide access to the porous section 106 of the implant 100. In some examples, this configuration promotes bone growth by enabling contact between the porous section 106 and select vertebral bodies. In some scenarios, this configuration facilitates the fusion between an inserted implant 100 and select bones in the disc space. In some embodiments, the size and shape of the of the hollow recesses 124 in the support section 108 vary. In the depicted example, the hollow recesses 124 are square-shaped. In any embodiment, the hollow recesses 124 may be formed in any geometrical shape including but not limited to circular, rectangular, triangular or any other shape, depending on the intended use of the implant 100. In some embodiments, the hollow recess 124 may be an indentation in a wall of the implant 100.

According to an embodiment of the present invention, the implant may be designed with a precise hollow tubular structure based on the implant's intended application. In some embodiments, the 3D matrix of the implant may be designed using computer-aided design ("CAD") techniques. In some embodiments, the tubular structure may be configured in a CAD model that can then be used to control 3D printing manufacturing process. Furthermore, the 3D matrix created by 3D printing methods can be tailored to create specific tube sizes and structures. Finally, the use of CAD models in conjunction with 3D printing, allows for the precise reproduction of identical implants. This was not possible with previous methods, such as the gas-evaporative method, which could not replicate implants with identical structures.

While multiple embodiments are disclosed, still other embodiments of the present invention will become apparent to those skilled in the art from this detailed description. There may be aspects of this invention that may be practiced without the implementation of some features as they are described. It should be understood that some details have not been described in detail in order to not unnecessarily obscure focus of the invention. The invention is capable of myriad modifications in various obvious aspects, all without departing from the spirit and scope of the present invention. It should be noted that the features illustrated in the drawings are not necessarily drawn to scale, and features of one embodiment may be employed with other embodiments as the skilled artisan would recognize, even if not explicitly stated herein. Accordingly, the drawings and descriptions are to be regarded as illustrative in nature and not restrictive.

What is claimed is:

1. An orthopedic implant comprising:
   a porous section formed from a first implant material, the porous section comprising,
      a porous inner portion for the promotion of bony ingrowth, and
      a non-porous wall forming a shell in which the porous inner portion is formed, wherein the non-porous wall has an opening on at least one face so that the porous inner portion is exposed to an outer surface of the orthopedic implant;
   a support section formed from a second implant material that provides structural support to the orthopedic implant, the support section comprising,
      one or more inner walls that define a chamber configured to retain the porous section, wherein the inner walls abut with the non-porous wall of the porous section, and
      one or more outer walls, wherein at least one of the outer walls is formed with a hollow recess; and
   a lattice structure extending from an outer surface of the non-porous wall of the porous section and into the inner walls of the support section.

2. The orthopedic implant of claim 1, wherein the non-porous wall is adapted to prevent the second implant material of the support section from penetrating the porous inner portion of the porous section.

3. An orthopedic implant comprising:
   a porous section formed of a first implant material, the porous section comprising,
      a three-dimensional matrix configured as a network of selectively interconnected nonuniform channels forming a nonuniform web consisting of a plurality of intersections that provide a porous region of varying porosity within the orthopedic implant for bony ingrowth, and
      a non-porous wall forming a shell around the three-dimensional matrix, wherein the non- porous wall has an opening on at least one face so that a portion of the three-dimensional matrix is exposed to an outer surface of the orthopedic implant; and
   a support section formed from a second implant material that provides structural support for the orthopedic implant, the support section comprising,
      an inner chamber configured to retain the porous section, wherein the inner chamber surrounds the non-porous wall of the porous section, and
      one or more outer walls, wherein at least one of the outer walls is formed with a recess that corresponds to the opening in the non-porous wall to enable contact between the portion of the three-dimensional matrix that is exposed by the opening in the non-porous wall and bone after the orthopedic implant is implanted.

4. The orthopedic implant of claim 3, further comprising a lattice structure extending from an outer surface of the non-porous wall of the porous section, wherein the lattice structure is configured to engage with interior walls of the support section.

5. The orthopedic implant of claim 4, wherein the lattice structure comprises a series of interconnected rods that penetrate into the inner chamber of the support section.

6. The orthopedic implant of claim 3, wherein the three-dimensional matrix protrudes beyond the opening of the non-porous wall.

7. The orthopedic implant of claim 5, wherein the support section is overmolded onto the porous section.

8. The orthopedic implant of claim 3, wherein the support section comprises at least two support section units that connect to enclose the porous section.

9. The orthopedic implant of claim 8, wherein the support section units are connected by one or more fasteners.

10. The orthopedic implant of claim 9, wherein the two support sections units are connected by the fasteners in two corners of the orthopedic implant.

11. The orthopedic implant of claim 3, wherein the non-porous wall of the porous section is adapted to prevent the second implant material of the support section from penetrating the three-dimensional matrix of the porous section.

12. An orthopedic implant comprising:
   a porous section comprising,
      a porous inner portion defined by a network of selectively interconnected nonuniform channels forming a nonuniform web consisting of a plurality of intersections that provide varying porosity within the orthopedic implant for bony ingrowth, and
      one or more non-porous exterior walls forming a shell around the porous inner portion, wherein a lattice structure extends from a surface of at least one of the one or more non-porous exterior walls; and
   a support section configured to retain the porous section and provide structural support for the orthopedic implant, the support section being formed with one or more hollow recesses, wherein at least one of the one or more hollow recesses is configured to enable contact between the porous inner portion of the porous section and bone after the orthopedic implant is implanted.

13. The orthopedic implant of claim 12, wherein at least one of the non-porous walls has an opening so that the porous inner portion is exposed to an outer surface of the orthopedic implant and the opening aligns with one of the one or more hollow recesses of the support section.

14. The orthopedic implant of claim 13, wherein the support section units are connected by one or more fasteners.

15. The orthopedic implant of claim 12, wherein the lattice structure comprises a series of interconnected rods that penetrate into the support section.

* * * * *